United States Patent
Gann et al.

(10) Patent No.: US 7,355,193 B2
(45) Date of Patent: Apr. 8, 2008

(54) DUST AND SCRATCH DETECTION FOR AN IMAGE SCANNER

(75) Inventors: Robert G Gann, Bellvue, CO (US); Kurt E. Spears, Fort Collins, CO (US)

(73) Assignee: Hewlett-Packard Development Company, L.P., Houston, TX (US)

(*) Notice: Subject to any disclaimer, the term of this patent is extended or adjusted under 35 U.S.C. 154(b) by 169 days.

(21) Appl. No.: 10/931,317

(22) Filed: Aug. 31, 2004

(65) Prior Publication Data
US 2005/0023492 A1 Feb. 3, 2005

Related U.S. Application Data

(62) Division of application No. 10/226,859, filed on Aug. 22, 2002, now abandoned, which is a division of application No. 09/629,495, filed on Jul. 31, 2000, now Pat. No. 6,465,801.

(51) Int. Cl.
*G01N 21/88* (2006.01)
(52) U.S. Cl. .............. 250/559.45; 250/559.4; 356/237.1
(58) Field of Classification Search ......... 250/559.4, 250/559.41, 559.42, 559.43, 559.44, 559.45, 250/559.07; 356/237.1, 237.2, 237.3, 237.4, 356/238.1
See application file for complete search history.

(56) References Cited

U.S. PATENT DOCUMENTS 6,064,478 A * 5/2000 Paul et al. ............... 356/237.1
2002/0051228 A1* 5/2002 Spears et al. ............... 358/445

* cited by examiner

*Primary Examiner*—Kevin Pyo
(74) *Attorney, Agent, or Firm*—Augustus W. Winfield

(57) ABSTRACT

Multiple scans of the same object are obtained, where for any given line on the object to be scanned, the angle of the illumination is different for each scan. The different scans are obtained from different rows of photosensors that are separated. Because the angles of illumination are different, the resulting shadows in each scan are different. The multiple scans may be combined into a single composite color image. In a composite image, a dust particle may generate a series of overlapping shadows, where each shadow is a different color. Searching the composite image for the unique pattern of colors may identify artifacts or defects. Alternatively, the data for one scanned image may be compared to the data for another scanned image, and any differences may be due to shadows, which may indicate defects.

3 Claims, 8 Drawing Sheets

DUST AND SCRATCH DETECTION FOR AN IMAGE SCANNER

RELATED APPLICATIONS

This application is a divisional application of U.S. patent application Ser. No. 10/226,859, filed Aug. 22, 2002 now abandoned, which is a divisional application of U.S. patent application Ser. No. 09/629,495, filed Jul. 31, 2000, which issued as U.S. Pat. No. 6,465,801, and which is hereby incorporated by reference.

FIELD OF INVENTION

This invention relates generally to devices for digital electronic scanning of images and more specifically to detection of dust and scratches and other surface defects.

BACKGROUND OF THE INVENTION

Electronic image scanners convert an optical image into an electronic form suitable for storage, transmission or printing. In a typical image scanner, light from an image is focused onto linear arrays of photosensors for scanning one line at a time. A two dimensional image is scanned by providing relative movement between the linear sensor arrays and the original image. For gray-scale scanning there may be only a single linear array of photosensors. In general, a color scanner measures the intensity of at least three relatively narrow bands of wavelengths of visible light, for example, bands of red, green and blue.

For image scanners, the digitized image may be degraded by the presence of artifacts on the surface of the object being scanned, such as dust and fingerprints, or defects in the surface of the object being scanned, such as scratches, folds, or textured surfaces. Multiple methods have been disclosed for detecting defects on transparent media. See, for example, U.S. Pat. Nos. 5,266,805, 5,969,372, and EP 0 950 316 A1. Some of the methods in the referenced patent documents utilize the fact that the dyes in transparent color film are essentially transparent to infrared light, whereas dust and scratches are relatively opaque. Other disclosed methods utilize dark field imaging, in which the light reaching the photosensors is reflected or diffracted by defects instead of the film.

Scanners for opaque media are configured differently than scanners for transmissive media, and different detection methods are needed. There is a need for automatically distinguishing surface artifacts and defects on reflective media.

SUMMARY OF THE INVENTION

Multiple scans of the same object are obtained, where for any given line on the object to be scanned, the angle of the illumination is different for each scan. The different scans are obtained from different rows of photosensors that are separated. Because the angles of illumination are different, the resulting shadows in each scan are different. The multiple scans may be combined into a single composite color image. In a composite image, a dust particle may generate a series of overlapping shadows, where each shadow is a different color. Searching the composite image for the unique pattern of colors may identify artifacts or defects. Alternatively, the data for one scanned image may be compared to the data for another scanned image, and any differences may be due to shadows, which may indicate defects.

DETAILED DESCRIPTION OF THE PREFERRED EMBODIMENT OF THE INVENTION

Figure 1:
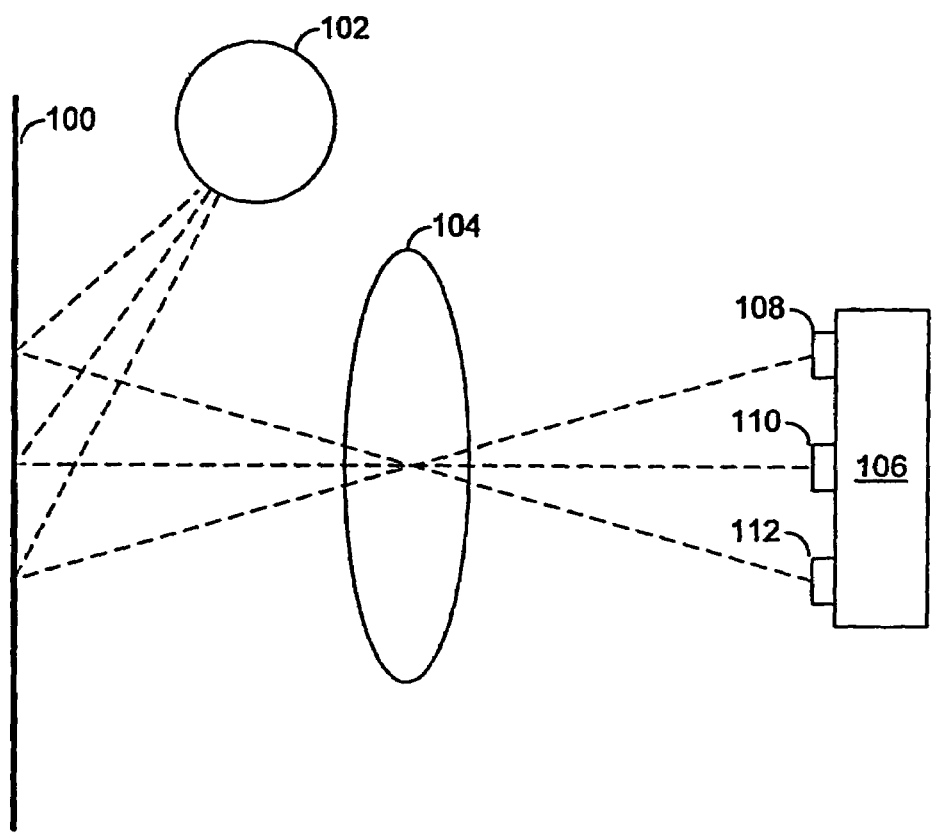
FIG. 1 is a simplified side view of an example configuration of a digital image scanner.

FIG. 1 illustrates an example configuration for a digital electronic image scanner. A document 100 is illuminated by a lamp 102. Light from the lamp 102 reflects from the document 100, passes through a lens 104, and impinges onto a photosensor assembly 106. The photosensor assembly 106 has three rows of photosensors (108, 110, 112), each filtered to receive a different range of wavelengths of light.

Figure 2:
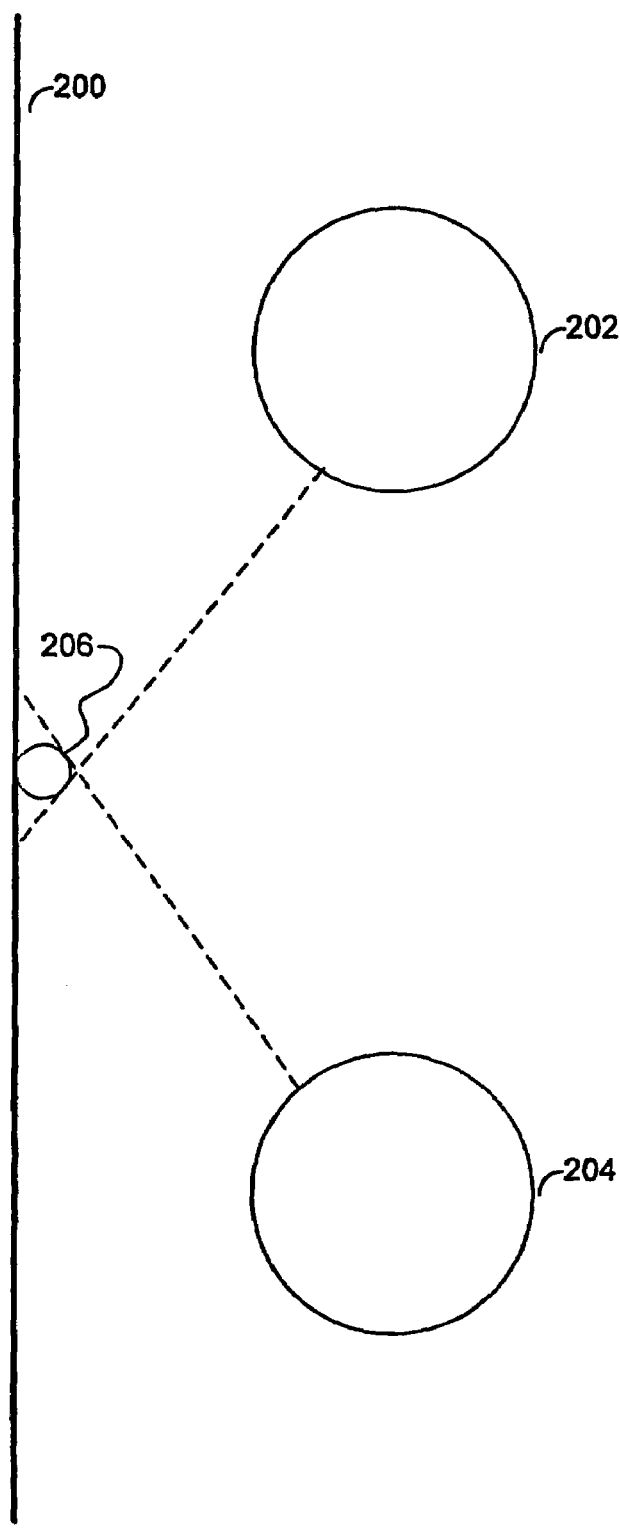
FIG. 2 is a simplified side view of a document being scanned with multiple light sources, illustrating how a dust particle casts a different shadow for each light source.

In FIG. 2, a document 200 is illuminated by one of two different light sources (202, 204). A dust particle 206 (exaggerated for illustration) is also illuminated. When dust particle 206 is illuminated by lamp 202, the particle casts a shadow downward. When dust particle 206 is illuminated by lamp 204, the particle casts a shadow upward. Assume that a first scan of document 200 is made with lamp 202 illuminated, and a second scan of document 200 is made with lamp 204 illuminated. If the data from the second scan is compared to data from the first scan, any differences may indicate shadows, which may indicate surface artifacts or defects.

Figure 3A:
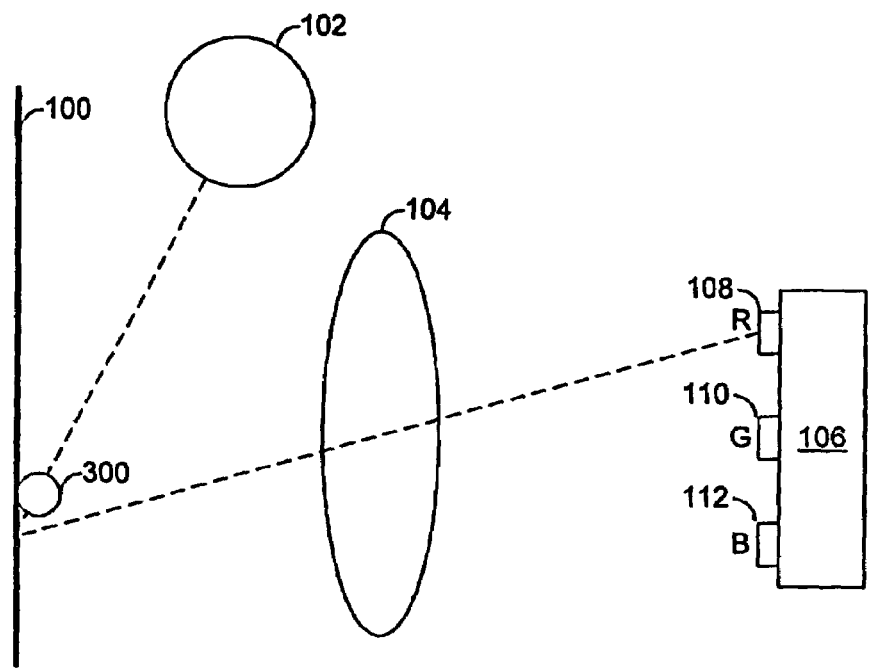
FIGS. 3A, 3B and 3C are simplified side views of a scanner as in FIG. 1, illustrating three positions of the scanner optics relative to a dust particle.
Figure 3B:
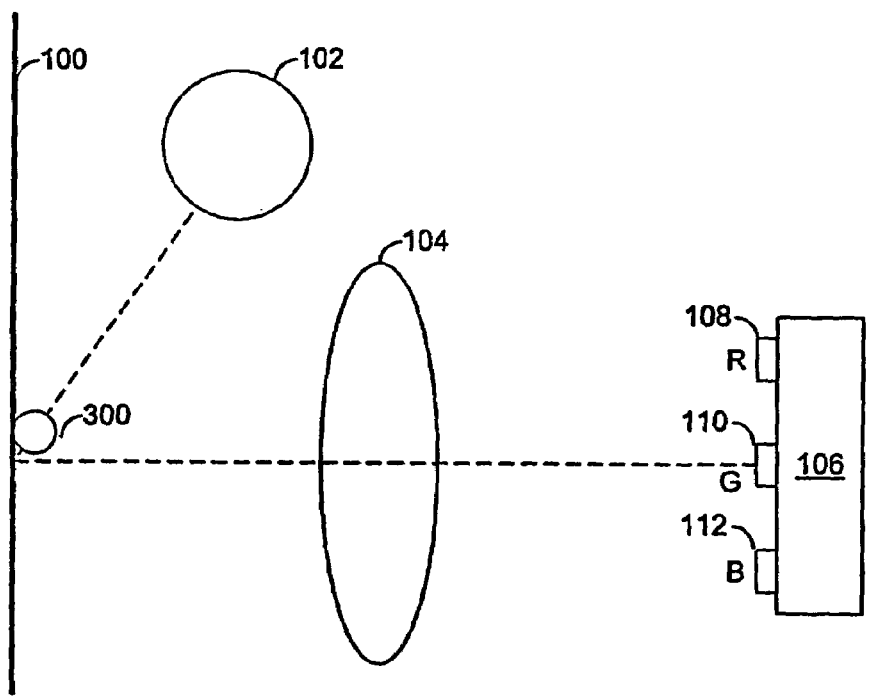
Figure 3C:
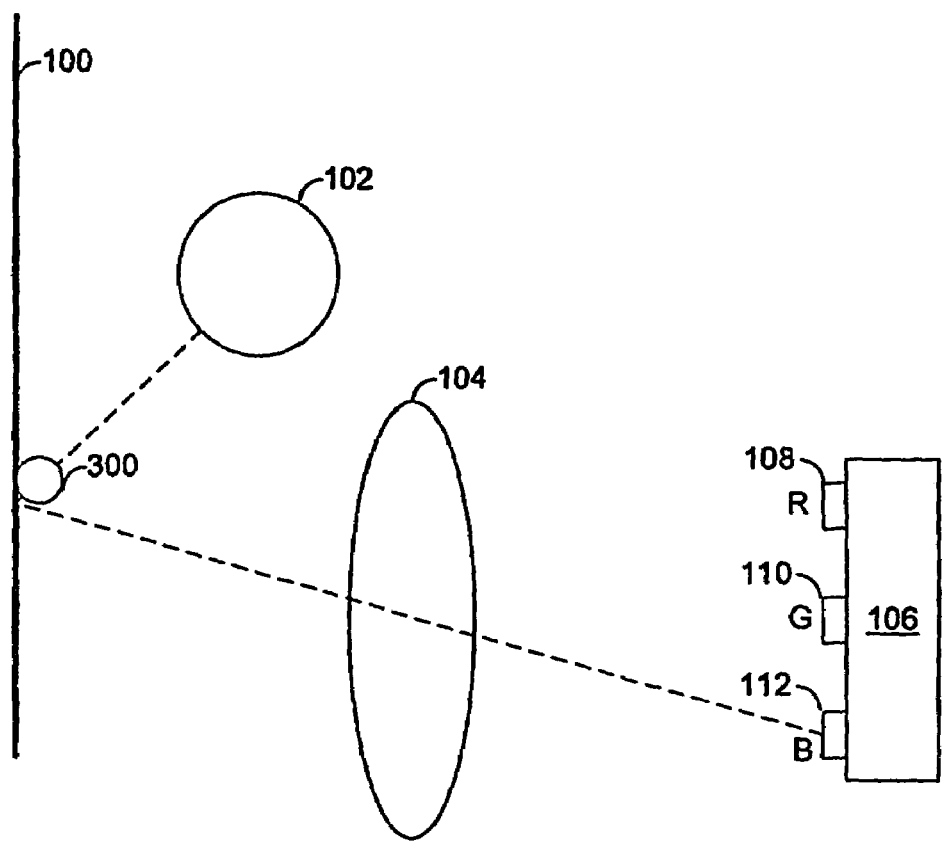

Instead of multiple lamps, one may use one lamp and multiple rows of photosensors. FIGS. 3A-3C illustrate a single lamp scanner as in FIG. 1 scanning a dust particle. In FIGS. 3A-3C, photosensor row 108 is assumed to sense red light, row 110 is assumed to sense green light, and row 112 is assumed to sense blue light. In FIG. 3A, a dust particle 300 is blocking light that would normally impinge on the red photosensor row 108. That is, photosensor row 108 is imaging a shadow. Assume that the document 100 is scanned by moving the lamp 102, the lens 104, and the photosensor assembly 106, relative to a stationary document 100, downward as viewed in FIG. 3A. In FIG. 3B, the lamp, lens, and photosensor assembly have moved downward relative to the document 100, and a shadow of the dust particle 300 is imaged by the green photosensor row 110. In FIG. 3C, the lamp, lens, and photosensor assembly have moved further downward, and a shadow of the dust particle 300 is imaged by the blue photosensor row 112. Note from the light ray traces that the shadow produced by the dust particle 300 will be slightly longer when scanned by the red photosensor row 108 than the shadow produced when scanned by the green photosensor row 110. Likewise, the shadow produced by the dust particle 300 will be slightly longer when scanned by the green photosensor row 110 than the shadow produced when scanned by the blue photosensor row 112.

Figure 4:
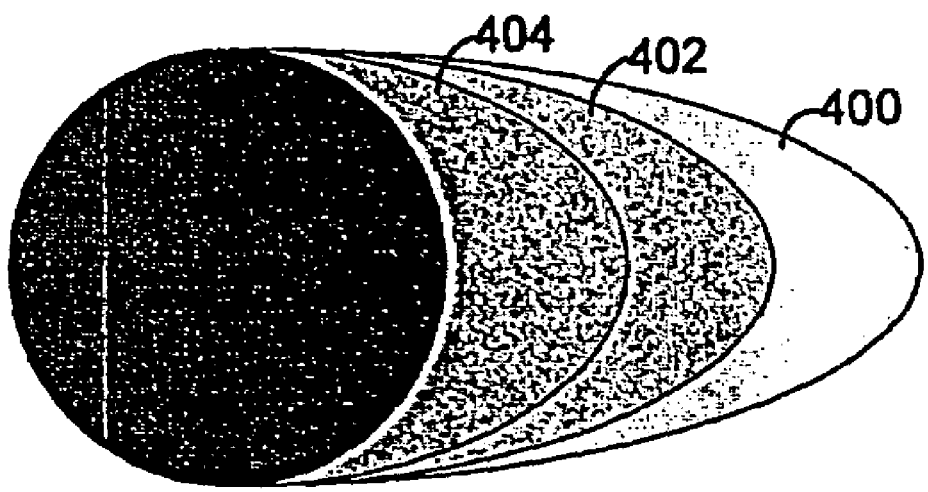
FIG. 4 is a plan view of an image, in a composite scan, of a dust particle that has been scanned with one lamp and three displaced rows of photosensors.

FIG. 4 illustrates an image of a dust particle and its shadows in a composite image using data from all three rows of sensors. The red photosensor row sees the longest shadow 400. If the document is white, the outer part of the shadow 400 in the composite image is cyan in color, because green and blue light are reflected but red is not reflected. The green photosensor row sees the next longest shadow 402, which has an outer area that is blue in color (assuming a white document, blue is reflected, but red and green are blocked). Finally, the blue photosensor row sees the shortest shadow 404, which is entirely gray or black. This distinctive pattern of colors in the composite image may indicate the presence of a defect. Of course, in a color composite image of a color document, the colors of the shadows are affected by the colors of the document. However, defects may still appear as small black or gray areas with a distinctive adjacent color pattern.

Figure 5:
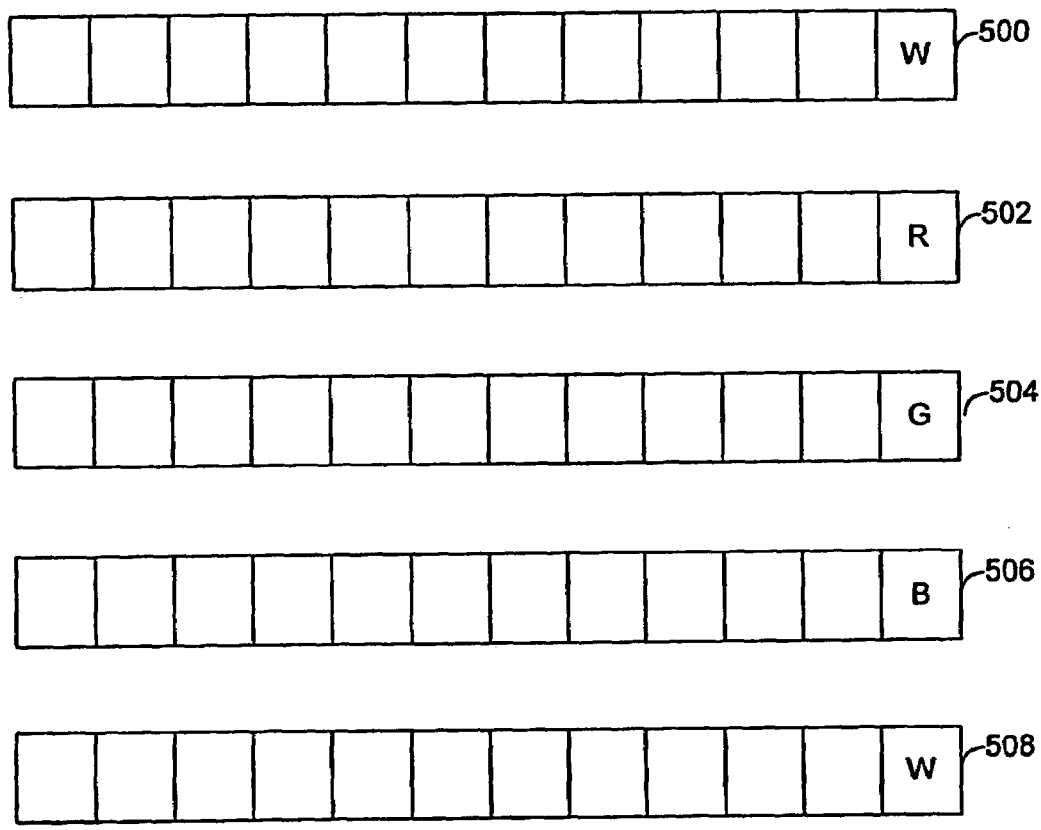
FIG. 5 is simplified plan view of a photosensor assembly having multiple photosensor arrays for one color.

Typically, for photosensor assemblies as illustrated in FIG. 1, the photosensor rows are relatively close together, making any shadow lengths and differences relatively small. Other photosensor configurations have been proposed in which there is an additional row of photosensors for white light. See, for example, U.S. Pat. No. 5,773,814. A row of photosensors for white light is useful for increasing the speed of scanning black-and-white documents, such as text. FIG. 5 illustrates an example of a photosensor assembly having two rows of photosensors for sensing white light. The two outer rows (500, 508) sense white light, and the three inner rows (502, 504, 506) sense red, green, and blue light. By adding a second white row, one can obtain two separate white scans, one with row 500 and one with row 508 and compare the two scans. The two white rows may be placed relatively far apart to increase the differences in shadow lengths.

Instead of two white rows, one could add a fourth colored row to a three-row photosensor assembly, where the fourth row senses light of the same color as one other row. For example, an additional green row could be added, and the two green scans could be compared for differences. Both scans are the same color, and any differences may indicate shadows, which may indicate artifacts or defects.

Figure 6:
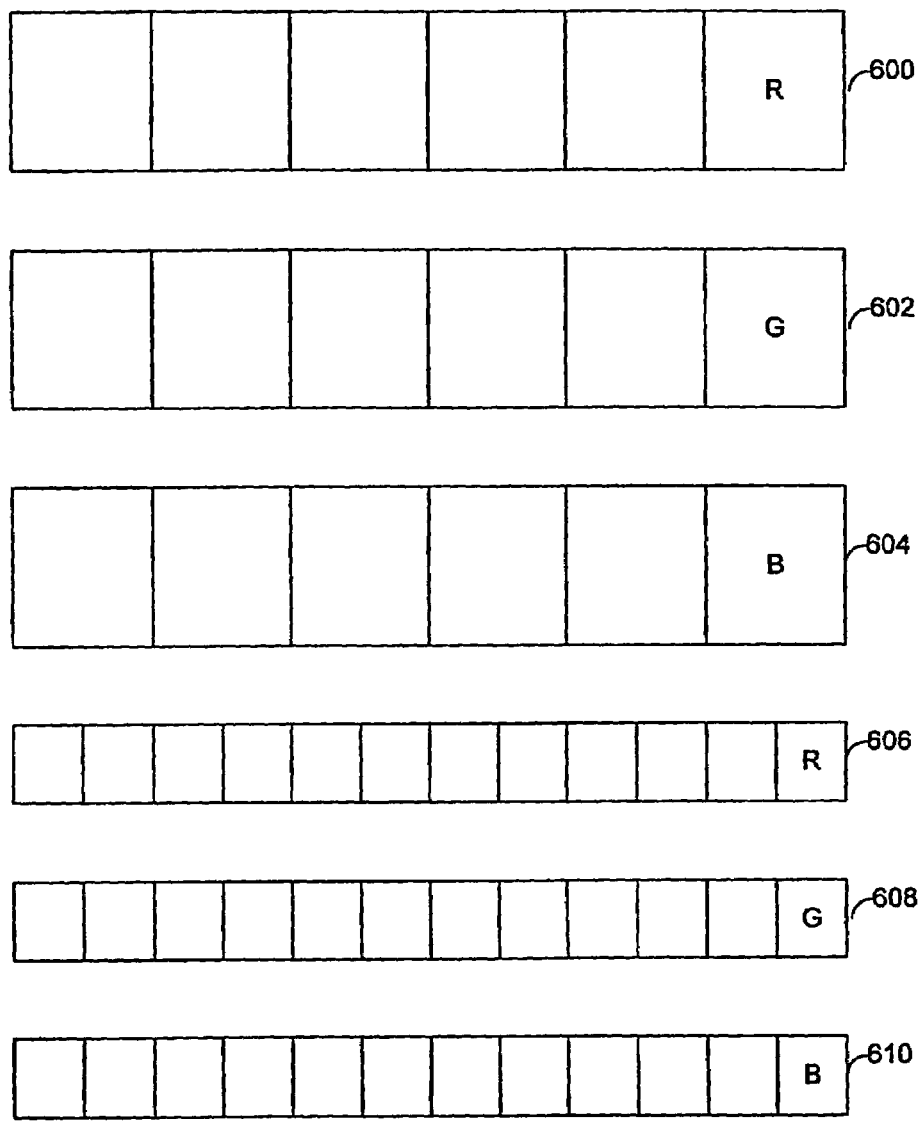
FIG. 6 is a simplified plan view of an alternative photosensor assembly having multiple photosensor arrays for one color.

Other photosensor configurations have been proposed in which there are two rows of photosensors for each color, where for each color, one row has relatively large photosensors and one row has relatively small photosensors. The lines with relatively small sensor areas are used for high native input sampling rates, and the lines with relatively large sensor areas are used for high color accuracy and speed. FIG. 6 illustrates an example of a photosensor assembly having three rows of relatively large photosensors (600, 602, and 604), and three rows of relatively small photosensors (606, 608, and 610). Each color band is sensed by one row of large photosensors and one row of small photosensors. For example, red wavelengths may be sensed by rows 600 and 606, green wavelengths may be sensed by rows 602 and 608, and blue wavelengths may be sensed by rows 604 and 610. A photosensor assembly as illustrated in FIG. 6 may used to detect shadows using two different scans of the same color. For example, a scan using photosensor row 600 may be compared to a scan using photosensor row 606. Both scans are the same color, and any differences may indicate shadows, which may indicate artifacts or defects.

Figure 7:
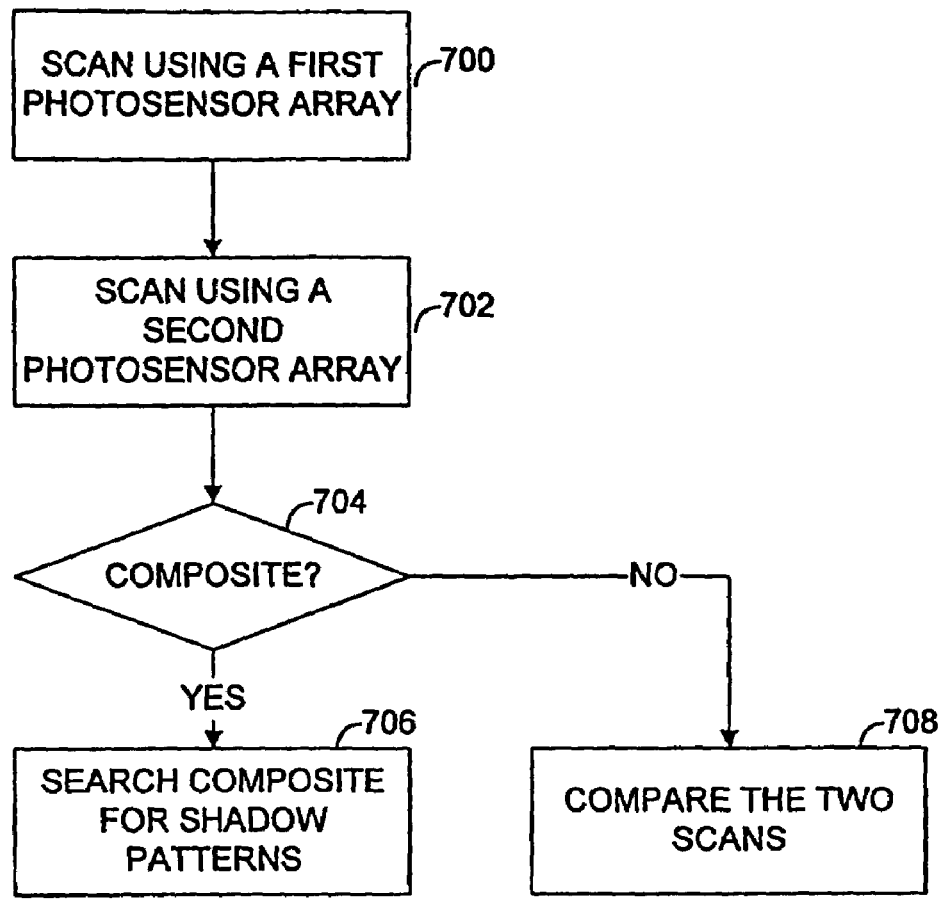
FIG. 7 is a flow chart of a method in accordance with the invention.

FIG. 7 is a flow chart illustrating a method in accordance with the invention. At steps 700 and 702, two scans are made with separate photosensor arrays (for example, separate rows within one assembly). If a composite image is formed (test 704), then the composite image may be searched for shadow patterns (step 706). Alternatively, separate scans may be compared to detect differences. Shadow patterns or differences may indicate shadows, which may indicate surface artifacts or defects.

Note that the above discussion has focused on dust, but scratches, textured surfaces, and even finger prints can generate shadows suitable for detection. In addition, note that there are many configurations of photosensor arrays, and the only requirement for the invention is to be able to generate and detect at least two different shadows.

The foregoing description of the present invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of detecting a defect on a surface being scanned, the method comprising:

scanning with a first scan an area on the surface with a light source and a first photosensor array;

scanning with a second scan the area on the surface with the light source and a second photosensor array; where the light source and first and second photosensor arrays are stationary relative to each other, the first and second photosensor arrays are spaced apart, and where there is relative movement between the light source and the area during the first and second scans and where an angle of the illumination of the first scan is different from the second scan;

determining that a defect is present in the area when the first and second scans are different;

determining that a defect is present in the area when an apparent shadow in the first scan has a different size in the second scan;

creating a composite image from the first and second scans; and searching the composite image for defects, where a defect is associated with a unique pattern of colors that generates a series of overlapping shadows, where each shadow is a different color.

2. The method of claim 1, further comprising:

where the first and second photosensor arrays detect substantially the same wavelengths of light.

3. The method of claim 1, further comprising:

where the first and second photosensor arrays detect different wavelengths of light, where the photosensor arrays are configured as plural rows of photosensors, each row being configured for sensing a different wavelength of light, where for each wavelength of light there exists at least one row of relatively large photosensors and at least one row of relatively small photosensors and where the relatively small photosensors are used for high native input sampling rates and the relatively large photosensor are used for high color accuracy and speed.

* * * * *